US008950270B2

(12) United States Patent
Williams et al.

(10) Patent No.: US 8,950,270 B2
(45) Date of Patent: Feb. 10, 2015

(54) SHORT BEAM SHEAR TEST FIXTURE

(75) Inventors: David L. Williams, Colleyville, TX (US); Ron McCullough, Burleson, TX (US)

(73) Assignee: Textron Innovatons Inc., Providence, RI (US)

( * ) Notice: Subject to any disclaimer, the term of this patent is extended or adjusted under 35 U.S.C. 154(b) by 395 days.

(21) Appl. No.: 13/347,488

(22) Filed: Jan. 10, 2012

(65) Prior Publication Data

US 2012/0222491 A1  Sep. 6, 2012

Related U.S. Application Data

(60) Provisional application No. 61/447,859, filed on Mar. 1, 2011.

(51) Int. Cl.
*G01N 3/02* (2006.01)
*G01N 3/04* (2006.01)
*B23B 31/16* (2006.01)

(52) U.S. Cl.
CPC .......... *G01N 3/04* (2013.01); *G01N 2203/0023* (2013.01); *G01N 2203/0048* (2013.01); *G01N 2203/0405* (2013.01); *G01N 2203/0435* (2013.01)
USPC .................. 73/856; 73/857; 73/859; 279/123

(58) Field of Classification Search
CPC ............ G01N 3/04; G01N 2203/0017; G01N 2203/04; G01N 2203/0405
USPC .............................. 73/856–860; 279/121–123
See application file for complete search history.

(56) References Cited

U.S. PATENT DOCUMENTS

| 3,224,259 | A | * | 12/1965 | De Nicola | 73/859 |
| 3,403,549 | A | * | 10/1968 | Griffin | 73/859 |
| 4,730,498 | A | * | 3/1988 | Blanch | 73/852 |
| 4,888,995 | A | * | 12/1989 | Curtis | 73/859 |
| 4,909,085 | A | * | 3/1990 | Hardy et al. | 73/859 |

(Continued)

FOREIGN PATENT DOCUMENTS

| JP | 60073431 A | 4/1985 |
| JP | 61219849 A | 9/1986 |
| JP | 62190437 A | 8/1987 |

OTHER PUBLICATIONS

Extended European Search Report Application No. 12153399.6-1234, issued by the European Patent Office on Apr. 25, 2012.

(Continued)

*Primary Examiner* — Lisa Caputo
*Assistant Examiner* — Jonathan Dunlap
(74) *Attorney, Agent, or Firm* — James E. Walton; Damon R. Hickman (57) ABSTRACT

The test fixture includes a housing, a first grip, and a second grip. The first grip and the second grip are each configured to clamp onto an upper surface and lower surface of a material coupon. The test fixture also includes an upper input jaw and a lower input jaw each configured to clamp onto the material coupon near a center of the upper surface and the lower surface of the material coupon. The test fixture is configured to load the material coupon in a first direction and a second direction. The first grip and the second grip are each configured to clamp onto the material coupon at a location which accordingly results in a desired testing ratio regardless of a variation in thickness of the material coupon.

18 Claims, 7 Drawing Sheets

(56) References Cited

U.S. PATENT DOCUMENTS

| | | | | |
|---|---|---|---|---|
| RE33,409 E | * | 10/1990 | Curtis | 73/859 |
| 7,540,201 B1 | * | 6/2009 | Hemmerlin | 73/856 |
| 7,793,553 B2 | * | 9/2010 | Lindeman | 73/856 |
| 7,827,868 B2 | * | 11/2010 | Lindeman | 73/859 |
| 2002/0166387 A1 | * | 11/2002 | Grote et al. | 73/857 |
| 2009/0139343 A1 | * | 6/2009 | Lindeman | 73/856 |
| 2010/0147694 A1 | | 6/2010 | Nardi | |

OTHER PUBLICATIONS

Leonard T et al: "An investigation into DTMA clamping problems", Measurement Science and Technology, 10P, Bristol, GB vol. 3, No. 3, Mar. 1, 1992, pp. 275-282.

Office Action dated May 28, 2014 from counterpart EP App. No. 12153399.6.

* cited by examiner

SHORT BEAM SHEAR TEST FIXTURE

GOVERNMENT LICENSE RIGHTS

This invention was made with government support under the NAVY, Contract No. N00019-06-G-0001, Work Order BF61. The government has certain rights in the invention.

BACKGROUND

1. Technical Field

The present application relates to a method and apparatus for testing material coupons.

2. Description of Related Art

Aerospace structures may be fabricated from a wide variety of materials. For example, composite materials are frequently used in aerospace structures due to their high strength to weight ratios. It is desirable to load test certain aerospace structures for verification that the structure will withstand the loading criteria. Typical prior art test fixtures require high tolerance material coupons in order to accurately test each coupon. Further, typical prior art test fixture lack the ability to reverse load test coupons.

Hence, there is a need for an improved test fixture for the testing of material coupons.

DESCRIPTION OF THE DRAWINGS

The novel features believed characteristic of the system of the present application are set forth in the appended claims. However, the system itself, as well as a preferred mode of use, and further objectives and advantages thereof, will best be understood by reference to the following detailed description when read in conjunction with the accompanying drawings, wherein:

DESCRIPTION OF THE PREFERRED EMBODIMENT

Illustrative embodiments of the system of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

The system of the present application includes a short beam shear test fixture 101, which is configured to apply reverse loading on a material coupon, which may also be referred to as a test coupon. Test fixture 101 is also configured to accommodate test coupons having a variety of lengths and widths while maintaining a desired length/thickness ratio between locations where the forces are bearing against the material coupon. The aforementioned features of the test fixture 101 are described further herein.

Referring to FIGS. 1-6, the test fixture 101 is illustrated. Test fixture 101 is configured to load test a material coupon 111. Material coupon 111 is material test specimen for which material properties may be analyzed. For example, the test fixture 101 is configured to subject dynamic reverse loading upon the material coupon 111. Afterwards, the material coupon 111 may be analyzed to determine non-failure, failure, failure mode, de-lamination, to name a few examples. In the preferred embodiment, material coupon 111 is fiberglass laminate sized at approximately 0.25 inch wide, 0.25 inch thick, and 1.75 inches long. However, it should be appreciated that material coupon 111 may be of a variety of materials and sizes.

Figure 6:
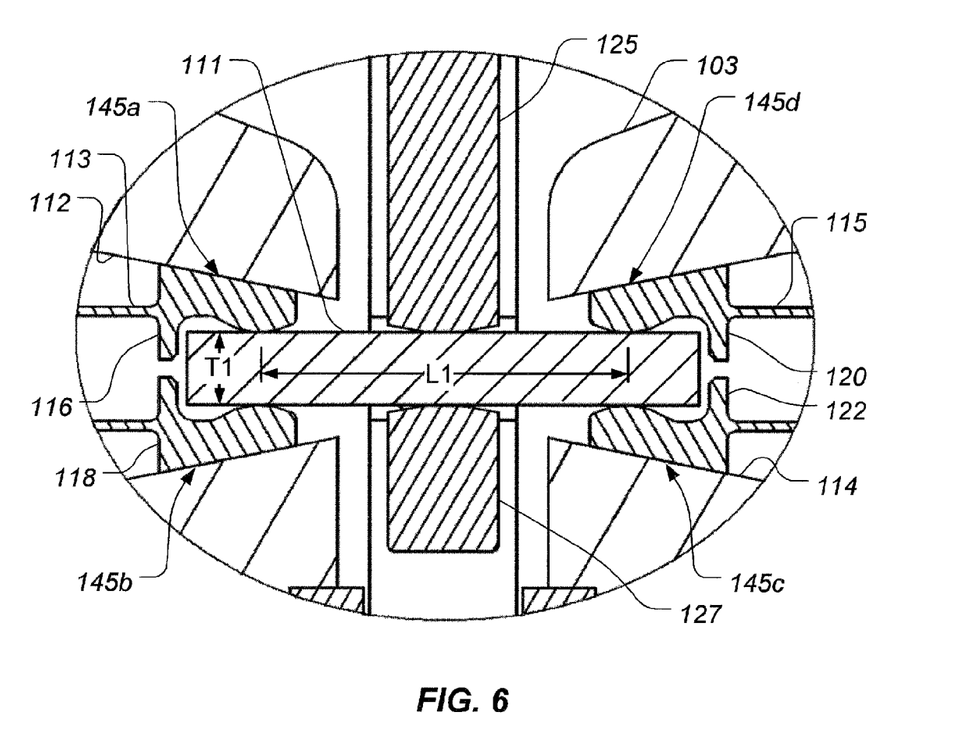
FIG. 6 is detail view of the test fixture, according to the preferred embodiment of the present application, taken at detail view callout VI in FIG. 3.

Test fixture 101 includes a housing 103 which provides a rigid structure for the various components. The material coupon 111 can be located approximately central in the housing 103. A first grip 113 and a second grip 115 are configured to secure the material coupon 111 on the upper and lower surfaces near each end portion so that a ratio of a testing length L1 to a testing thickness T1 is a representation of a specified testing ratio. As shown in FIG. 6, the testing length L1 is the length of the material coupon located between the grip contact locations. The testing thickness T1 is the thickness of the material coupon 111. In the preferred embodiment, the specified testing ratio is 5:1, such that the testing length L1 is fives times the magnitude of the testing thickness T1. For example, if testing ratio of 5:1 is desired, then a material coupon 111 having a testing thickness T1 of 0.25 inch would result in a desired testing length L1 of 1.25 inches. However, test fixture 101 can be configured to test material coupons at other testing ratios. For example, test fixture 101 can be configured to test material coupons at a 4:1 testing ratio.

Test fixture 101 is configured to maintain the specified testing ratio even when the thickness T1 of the material coupon 111 represents a deviation from the nominal thickness.

For example, if the material coupon 111 has a thickness T1 that is thicker than the nominal thickness, then the first grip 113 and the second grip 115 clamp the material coupon 111 further away from the center of the material coupon 111. Conversely, if the material coupon 111 has a thickness T1 that is thinner than nominal, the first grip 113 and the second grip 115 clamp the material coupon further in towards the center of the material coupon 111. Such a feature prevents the material coupon 111 from having to hold a very tight nominal thickness. Therefore, the material coupon 111 can be efficiently fabricated without being subject the high cost of maintaining a tight nominal thickness.

First grip 113 includes an upper grip member 116 and a lower grip member 118. Upper grip member 116 and lower grip member 118 extend from a main body portion of first grip 113 that allows the upper grip member 116 and lower grip member 118 to flex in a direction normal to the clamping surface of the material coupon 111. Similarly, second grip 115 includes an upper grip member 120 and a lower grip member 122. Upper grip member 120 and lower grip member 122 extend from a main body portion of second grip 115 that allows the upper grip member 120 and lower grip member 122 to flex in a direction normal to the clamping surface of the material coupon 111.

The specified testing ratio is maintained by the slope surfaces 145a and 145b, which define mating surfaces of a first interior portion 112 of housing 103, to the bearing surfaces of upper grip member 116 and lower grip member 118 of first grip 113. Similarly, the specified testing ratio is maintained by slope surfaces 145c and 145d, which define mating surfaces of a second interior portion 114 of housing 103, to the bearing surfaces of upper grip member 120 and lower grip member 122 of second grip 115. Slope surfaces 145a-145d have a slope angle that is representative of the specified testing ratio, such as a 5:1 slope. In the illustrated embodiment, slope surfaces 145a-145d are planar mating surfaces of the grips 113 and 115, and the housing 103; however, an alternative embodiment may include non-planar features that nonetheless mate at planar slope surfaces 145a-145d. For example, bearing surfaces of upper grip member 116 and lower grip member 118 of first grip 113, as well as upper grip member 120 and lower grip member 122 of second grip 115, can include non-planar features, such as ridges, that define bearing surfaces where the ridges mate with interior portions of housing 103 at slope surfaces 145a-145d. Similarly, the interior portions of housing 103 can have non-planar features, such as ridges, that define bearing surfaces where the ridges mate with the bearing surfaces of upper grip member 116 and lower grip member 118 of first grip 113, as well as the bearing surfaces of upper grip member 120 and lower grip member 120 second grip 115.

During a test operation, a material coupon 111 is inserted into test fixture 101 such that the first grip 113 and the second grip 113 are clamped onto the material coupon 111. The exact location of clamping onto the material coupon 111 depends on the actual thickness of the specific material coupon 111 being tested. A first compression spring 117 applies a force to the first grip 113 so that first grip 113 clamps onto material coupon 111. Similarly, a second compression spring 119 applies a force to the second grip 115 so that the second grip 113 clamps onto material coupon 111. The upper grip member 116 and lower grip member 118 of first grip 113, as well as upper grip member 120 and lower grip member 122 of second grip 115, self adjust by flexing vertically while moving horizontally until clamping onto material coupon 111 and bearing against housing 103 at slope surfaces 145a-145d. A first grip adjustment knob 121 and a second grip adjustment knob 123 are each configured so that a user can adjust the clamping force applied to the material coupon 111 from the first grip 113 and the second grip 115, respectively. Each of first compression spring 117 and second compression spring 119 induces continuous clamping pressure on material coupon 111. Though first compression spring 117 and second compression spring 119 each produce a non-normal force, the bearing of first grip 113 and the second grip 115 against a first interior portion 112 and second interior portion 114 of housing 103 at slope surfaces 145a-145d converts the spring forces into clamping forces normal to the upper and lower surfaces of material coupon 111.

Test fixture 101 further includes an upper input jaw 125 and a lower input jaw 127 configured to apply a clamping force at the center of the upper and lower surfaces of the material coupon 111. In the preferred embodiment, the upper input jaw 125 and lower input jaw 127 are at least partially housed within an input guide plate 107 and an input clamp plate 109. A cam block 129 is loaded in a direction 137 by a biasing element 131 and a fastener 133. In the preferred embodiment, biasing element 131 is a plurality of Belleville washers oriented to provide a spring force. It should be appreciated that biasing element 131 may be of a wide variety of biasing elements, such a compression spring, or the like. The loading in direction 137 loads upper jaw input 125 in a direction 139, thereby inducing a constant clamping force on material coupon 111. Such a contact clamping force accounts for any wear upon material coupon 111 during the test. The clamping force can be adjusted by adding or removing Belleville washers in biasing element 131. A shim 141, and other components, may be used to locate the material coupon 111 on a center depthwise in the test fixture 101. A gap 143 may be desirable so that material coupon 111 isn't compressed by the shim 141.

Figure 7:
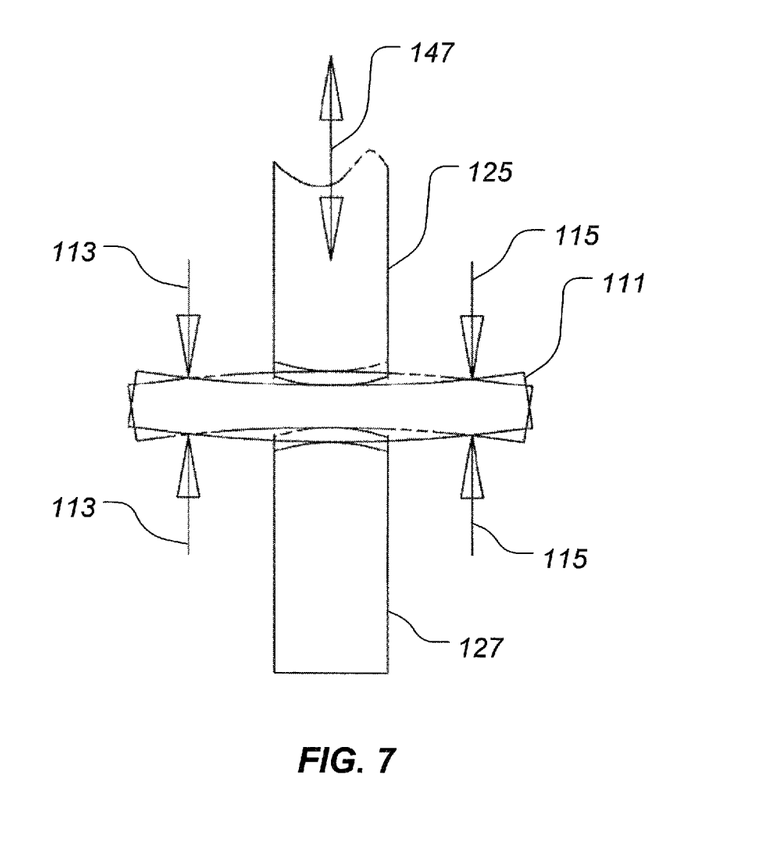
FIG. 7 is schematic view illustrating the testing of a material coupon in the test fixture, according to the preferred embodiment of the present application.

Upper input jaw 125 and lower input jaw 127 are operably associated with an adapter 105. An input guide 135 may be used to provide a bearing surface to keep upper input jaw 125 and lower input jaw 127 centered in test fixture 101. The adapter 105 is configured for attachment to a loading device. In the preferred embodiment, the loading device has hydraulic arms which clamp onto the adapter 105. During a test, the loading device loads the material coupon 111, via the adapter 105. Because the material coupon 111 is continuously clamped on the upper and lower surfaces by the first grip 113, the second grip 115, the upper input jaw 125, and the lower input jaw 127, the loading device can subject the material coupon 111 to reverse loading. Referring now to FIG. 7, the reverse loading of material coupon 111 is schematically illustrated. Reverse loading is the positive and negative loading of test material coupon 111 in the directions shown by a reverse loading direction 147. The reverse loading procedure may entail the loading of material coupon 111 at a variety of frequencies. However, the preferred embodiment includes performing reverse loading at a frequency of approximately 20-30 hertz. The reverse loading capability of test fixture 101 allows the material coupon 111 to be continuously loaded along direction 147. It should be appreciated that the amount of deflection, as schematically illustrated in FIG. 7, is dependent in part upon the material of the of the material coupon 111, as well as the amount of load applied by loading device.

Figure 8:
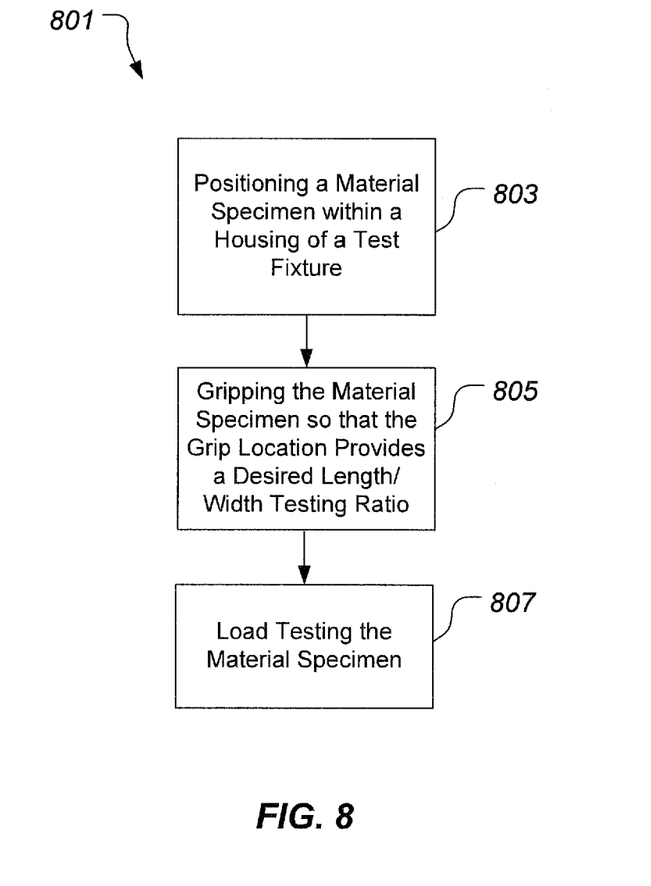
FIG. 8 is a schematic view of a method for load testing a material coupon, according to an illustrative embodiment of the present application.

Referring to FIG. 8, a method 801 of load testing material coupon 111 in test fixture 101 is schematically illustrated. Method 801 is schematically illustrated to include steps 803, 805, and 807; however, it should be appreciated that method 801 can include any steps and procedures described herein with regard to test fixture 101 in FIGS. 1-7. Step 803 can include positioning material coupon 111 within housing 103.

Figure 1:
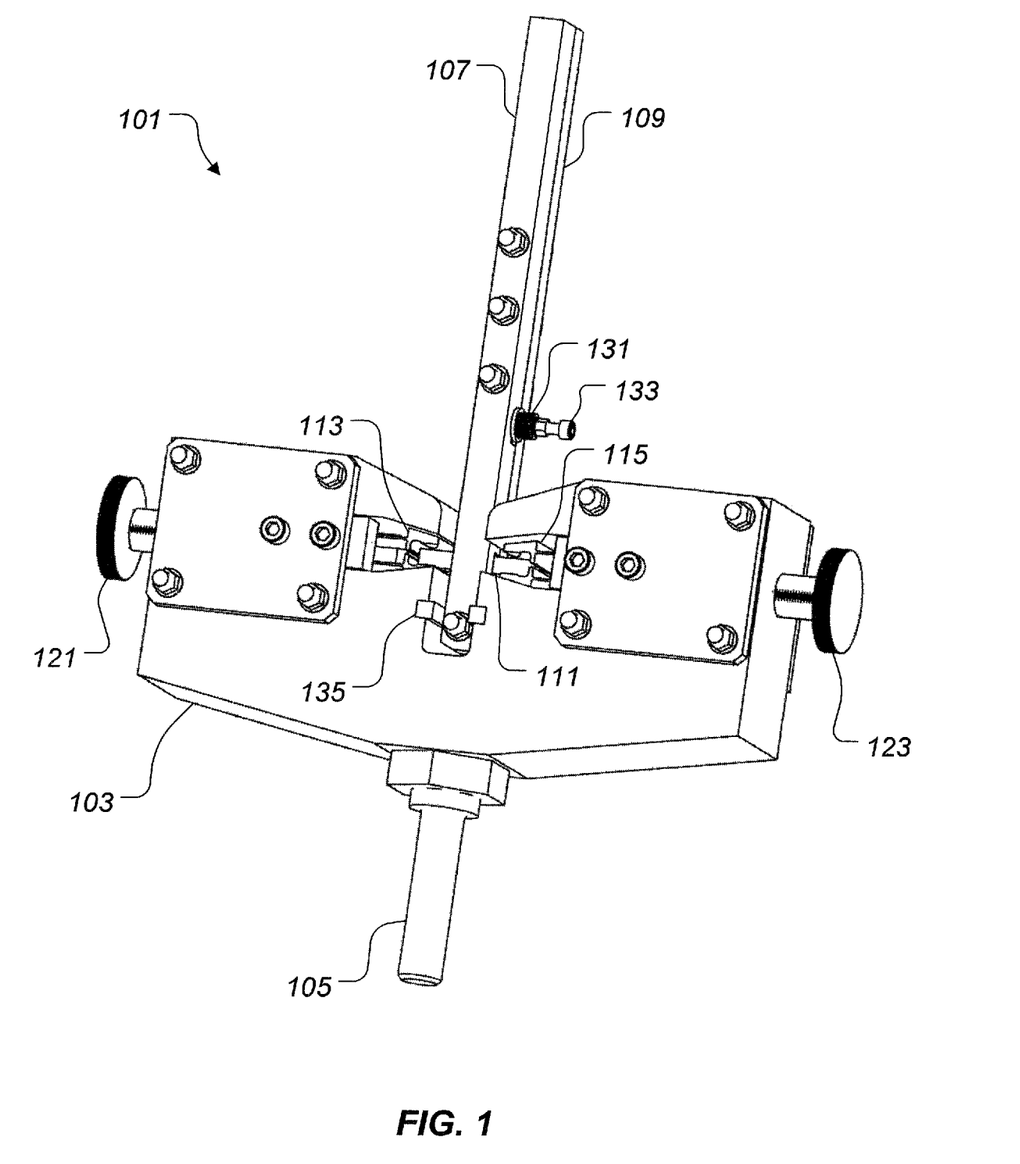
FIG. 1 is a perspective view of a test fixture, according to the preferred embodiment of the present application.
Figure 2:
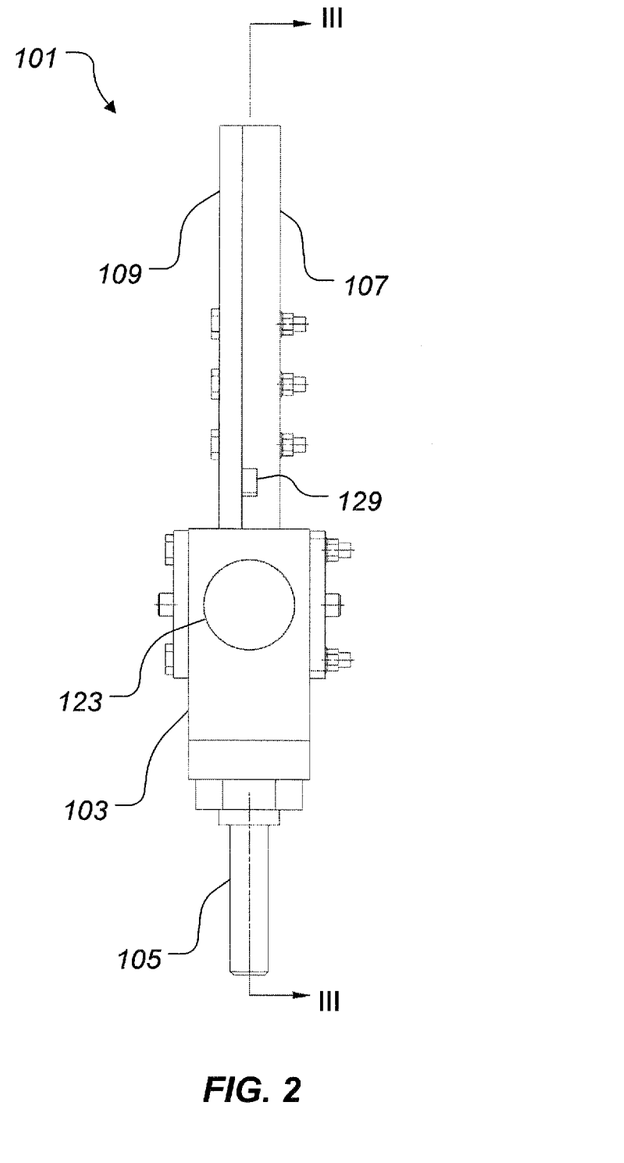
FIG. 2 is side view of the test fixture, according to the preferred embodiment of the present application.
Figure 3:
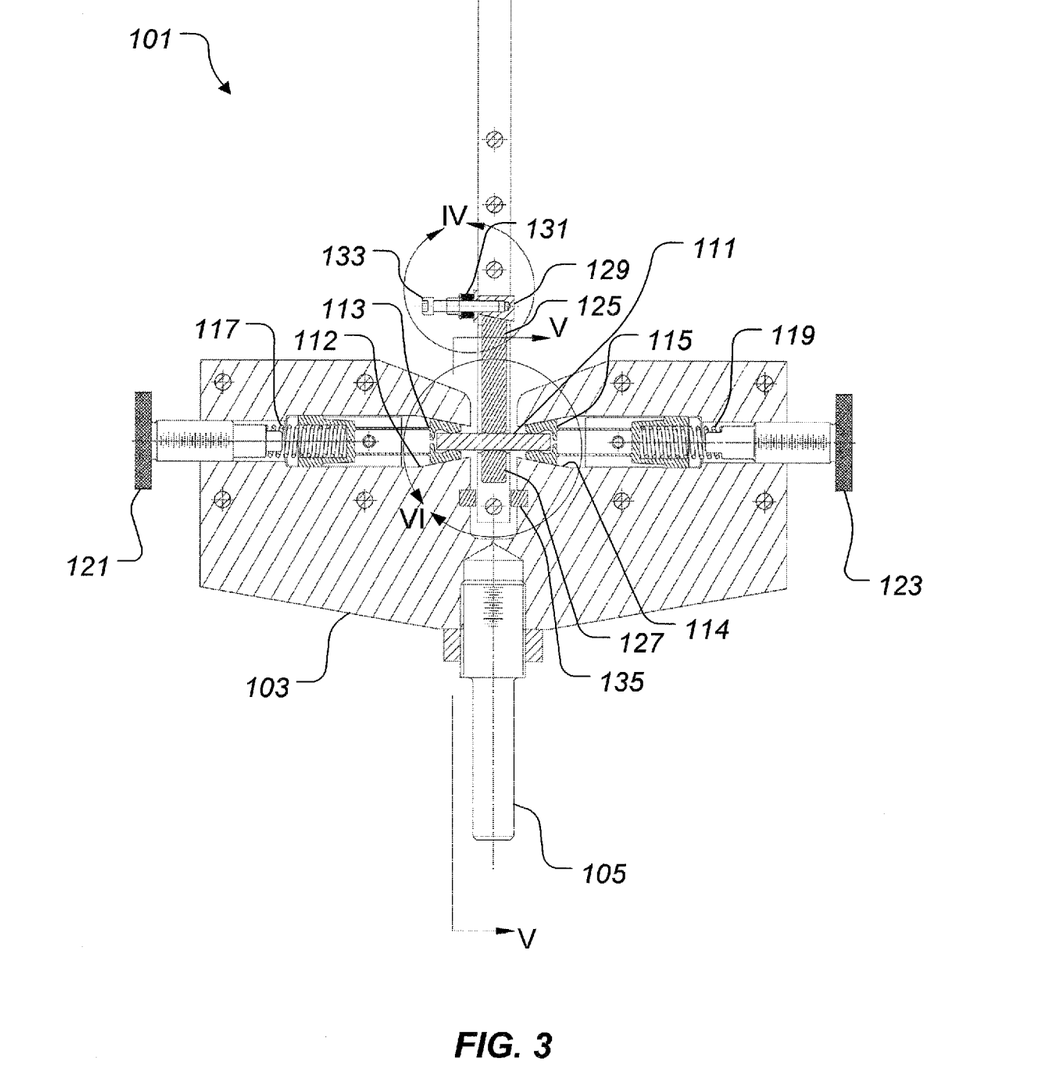
FIG. 3 is cross sectional view of the test fixture, according to the preferred embodiment of the present application, taken at section lines III-III in FIG. 2.
Figures 4, 5:
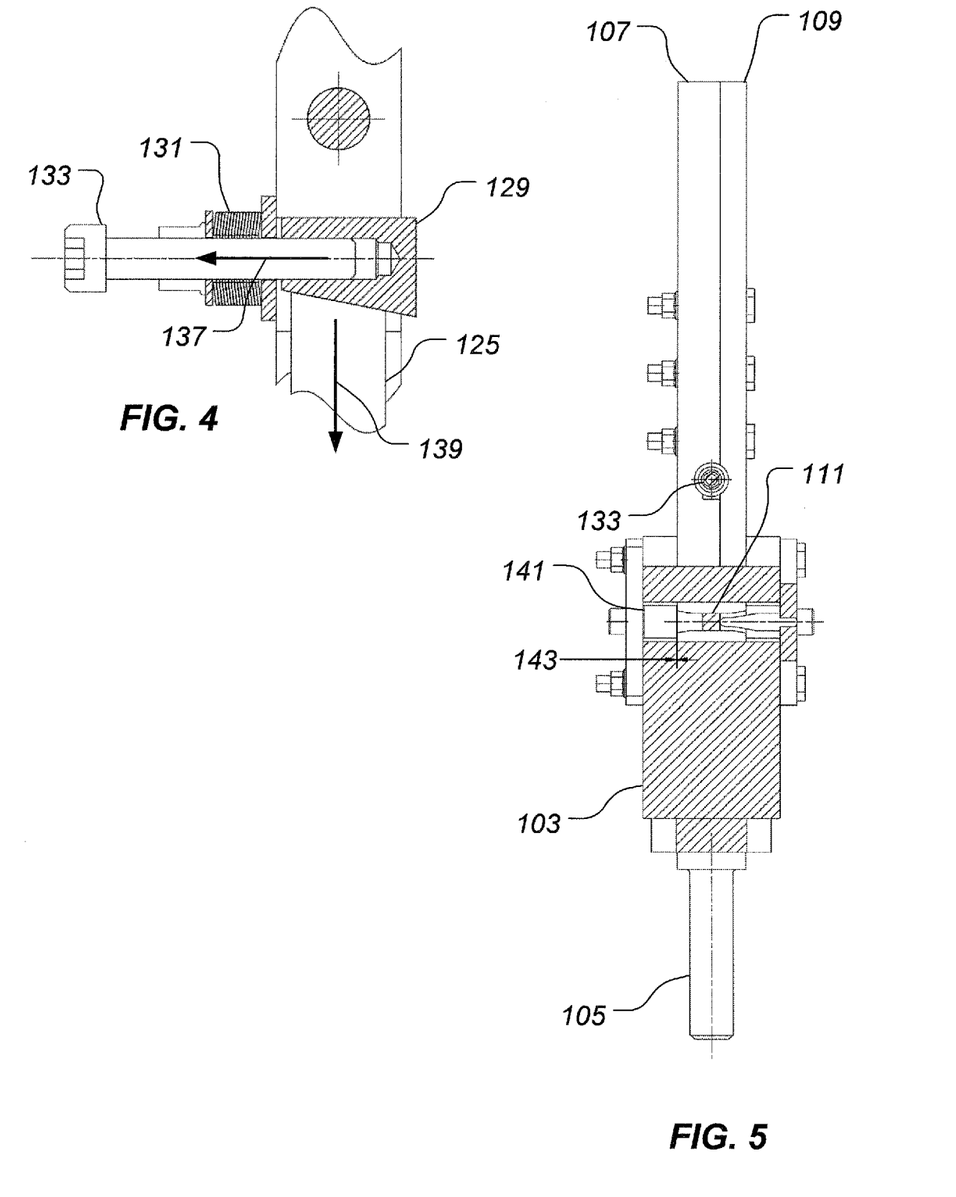
FIG. 4 is detail view of the test fixture, according to the preferred embodiment of the present application, taken at detail view callout IV in FIG. 3.
FIG. 5 is cross sectional view of the test fixture, according to the preferred embodiment of the present application, taken at section lines V-V in FIG. 3.

More specifically, material coupon 111 can be located within first interior position 112 and second interior position 114, as shown in FIGS. 3 and 6. Step 805 can include gripping material coupon 111 so that the grip location provides a desired length/width testing ratio. For example, first grip 113 is translated so that the bearing surfaces act to clamp together upper grip member 116 and lower grip member 118 until material coupon 111 is clamped at a first grip location. Similarly, second grip 115 is translated so that the bearing surfaces act to clamp together upper grip member 120 and lower grip member 122 until material coupon 111 is clamped at a second grip location. The bearing surfaces, such as slope surfaces 145a-145d have a slope angle indicative of the desired length:width testing ratio of material coupon 111. In the illustrated embodiment, slope surfaces 145a-145d have a slope angle of 5:1 (L1:T1); however, it should be fully appreciated that slope surfaces 145a-145d may be configured with other slope angles. Step 807 includes loading testing material coupon 111. For example, step 807 can include reverse loading material coupon 111 such that material coupon 111 is subjected to loading in a first direction and a second direction. During this testing procedure, first grip 113, second grip 115, upper input jaw 125, and lower input jaw 127 provided continuous clamping pressure on the upper and lower surfaces of material coupon 111.

The test fixture 101 provide significant advantages, including: 1) enabling the reverse loading of a material coupon; and 2) ability to accommodate a material coupon that has a thickness which deviates from a nominal thickness by automatically adjusting the location where the first and second grips clamp to the material coupon.

The particular embodiments disclosed above are illustrative only, as the system of the present application may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the application. Accordingly, the protection sought herein is as set forth in the claims below. It is apparent that a system with significant advantages has been described and illustrated. Although the system of the present application is shown in a limited number of forms, it is not limited to just these forms, but is amenable to various changes and modifications without departing from the spirit thereof.

The invention claimed is:

1. A test fixture for load testing a material coupon, the test fixture comprising:
   a housing having a first interior portion and a second interior portion;
   a first grip configured to clamp onto an upper surface and a lower surface at a first end portion of the material coupon, the first grip further being configured to mate against the first interior portion of the housing at a first upper slope surface and a first lower slope surface;
   a second grip configured to clamp onto the upper surface and the lower surface at a second end portion of the material coupon, the second grip further being configured to mate against the second interior portion of the housing at a second upper slope surface and a second lower slope surface;
   an input jaw configured to clamp onto the material coupon near a center portion of the material coupon;
   wherein the first upper slope surface, the first lower slope surface, the second upper slope surface, and the second slope surface each have a slope angle that causes the first grip and the second grip to contact the material coupon at a length location that is dependent upon a thickness of the material coupon;
   wherein the first grip is configured to clamp onto the upper surface and the lower surface at the first end portion of the material coupon with a clamping force, the clamping force being adjustable by a first grip adjustment knob; and
   wherein the first grip adjustment knob is configured to adjust a first compression spring that provides a spring force against a body portion of the first grip.

2. The test fixture according to claim 1, wherein the slope angle is similar to a desired testing ratio, the desired testing ratio being ratio of the length location to the thickness of the material coupon.

3. The test fixture according to claim 2, wherein the slope angle is 5:1.

4. The test fixture according to claim 1, the input jaw comprising an upper input jaw configured to contact the upper surface of the material coupon, and a lower input jaw configured to contact the lower surface of the material coupon.

5. The test fixture according to claim 1, wherein the input jaw is coupled to a loading device, the loading device being configured to subject the material coupon to loading in a first direction and in a second direction that is opposite to the first direction.

6. The test fixture according to claim 1, wherein the input jaw is coupled to a loading device, the loading device being configured to apply a reciprocating load at a frequency.

7. The test fixture according to claim 1, wherein the input jaw clamps onto the material coupon with an input clamping force, the input clamping force being applied by a biasing element.

8. The test fixture according to claim 7, wherein the biasing element causes the input clamping force to be constant during a test procedure.

9. A test fixture, for load testing a material coupon, the test fixture comprising:
   a housing;
   a first grip and a second grip each configured to clamp onto an upper surface and lower surface of the material coupon with a clamping force, the clamping force being adjustable by a first grip adjustment knob; and
   an upper input jaw and a lower input jaw configured to clamp onto the material coupon near a center of the upper surface and the lower surface of the material coupon;
   wherein the test fixture is configured to alternately load the material coupon in a first direction and a second direction; and
   wherein the first grip adjustment knob is configured to adjust a first compression spring that provides a spring force against a body portion of the first grip.

10. The test fixture according to claim 9, wherein the first grip and the second grip are each configured to clamp onto the material coupon at a location which accordingly results in a desired testing ratio regardless of the thickness of the material coupon.

11. The test fixture according to claim 10, wherein the testing ratio is the ratio of a length of the material coupon between the first grip and the second grip, and the thickness of the material coupon.

12. The test fixture according to claim 9, wherein the upper input jaw and the lower input jaw clamp onto the material coupon with an input clamping force, the input clamping force being applied by a biasing element.

13. The test fixture according to claim 12, wherein the biasing element is configured to make the clamping force continuous so as to compensate for any wear on the material coupon.

14. The test fixture according to claim 9, wherein the housing has a first interior portion and a second interior portion, the first interior portion and the second interior portion each having a slope surface at a slope angle that is similar to a desired testing ratio, the desired testing ratio being the a ratio of a test length of the material coupon to a width of the material coupon, the test length being a length of the material coupon located between the first grip and the second grip.

15. A method of load testing a material coupon in a test fixture, the method comprising:

positioning the material coupon within a housing of the test fixture;

gripping the material coupon so that a first grip location and a second grip location provide a desired length:width testing ratio of the material coupon;

adjusting a clamping force of the material coupon by a first grip adjustment knob; and load testing the material coupon in the test fixture, wherein the first grip adjustment knob is configured to adjust a first compression spring that provides a spring force against a body portion of the first grip.

16. The method according to claim 15, wherein the step of gripping the material coupon so that the first grip location and the second grip location provide a desired length:width testing ratio of the material coupon includes translating the first grip and the second grip so as to bear against an inner portion of the housing, the inner portion of housing having a slope surface that has a slope angle indicative of the desired length:width testing ratio of the material coupon.

17. The method according to claim 15, wherein the step of load testing the material coupon in the test fixture includes a reverse loading of the material coupon.

18. The method according to claim 15, further comprising:

clamping a load input jaw near a center of an upper surface and a lower surface of the material coupon.

\* \* \* \* \*